US00PP31080P2

(12) United States Plant Patent
Bradford et al.

(10) Patent No.: US PP31,080 P2
(45) Date of Patent: Nov. 19, 2019

(54) PEACH TREE NAMED 'PEARL PRINCESS II'

(50) Latin Name: *Prunus persica*
Varietal Denomination: Pearl Princess II

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 16/350,705

(22) Filed: Dec. 26, 2018

(51) Int. Cl.
*A01H 5/08* (2018.01)
*A01H 6/74* (2018.01)

(52) U.S. Cl.
USPC ..... Plt./196
CPC ..... *A01H 6/74* (2018.05)

(58) Field of Classification Search
USPC ..... Plt./196
CPC ..... A01H 5/0868
See application file for complete search history.

(56) References Cited

U.S. PATENT DOCUMENTS

PP12,570 P2 4/2002 Bradford
PP18,771 P2 4/2008 Bradford
PP28,505 P3 10/2017 Bradford

*Primary Examiner* — Kent L Bell

(57) ABSTRACT

The present invention relates to a new and distinct variety of peach tree, *Prunus persica*, broadly characterized by a large size, vigorous, hardy, self-fertile, productive and regular bearing tree. The variety blooms during mid season and requires about 525 chilling hours. The fruit matures under the ecological conditions described in mid June, with first picking on Jun. 14, 2018. The fruit is uniform, medium in size, globose in shape, freestone in type, firm and crisp in texture, mostly red in skin color, white in flesh color, and sub-acidic in flavor.

1 Drawing Sheet

Botanical classification: *Prunus persica.*
Variety denomination: 'PEARL PRINCESS II'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of peach tree, which has been denominated varietally as 'Pearl Princess II'.

The present variety was hybridized by us in 2007 as a first generation cross using 'Snow Princess' (U.S. Plant Pat. No. 12,570) peach as the selected seed parent and 'May Princess' (U.S. Plant Pat. No. 18,771) peach as the selected pollen parent. Upon reaching maturity the fruit of this cross was gathered, and the seeds were removed, cracked, stratified, germinated, and grown as seedlings on their own root in our greenhouse. Upon reaching dormancy the seedlings were transplanted as a group to a cultivated area of our experimental orchard located near Le Grand, Calif., in Merced County (San Joaquin Valley). During the fruit evaluation season of 2012 we selected the present variety as a single tree from the group of seedlings described above. Subsequent to origination of the present variety of peach tree, we asexually reproduced it by budding and grafting in the experimental orchard described above, and such reproductions were true to the original tree in all respects. The reproduction of the variety included the use of 'Nemaguard' (unpatented) rootstock upon which the present variety was compatible and true to type.

The present variety is similar to its seed parent, 'Snow Princess' (U.S. Plant Pat. No. 12,570) peach, by having showy blossoms, by being self-fertile, and by producing peaches that are mostly red to pink in skin color, white in flesh color, globose in shape, and freestone in type, but is quite distinguished therefrom by blooming about five days later, by having a higher chilling requirement, by having globose instead of reniform leaf glands, and by producing fruit that is somewhat smaller in size and that ripens about forty-eight days earlier.

The present variety is similar to its pollen parent, 'May Princess' (U.S. Plant Pat. No. 18,771) peach, by having showy blossoms, by being self-fertile, and by producing peaches that are mostly red in skin color and firm in texture, but is quite distinguished therefrom by having globose instead of reniform leaf glands, by blooming about a week later, by requiring more chilling hours, and by producing fruit that is freestone instead of clingstone in type, that is globose instead of oblate in shape, that is much less acidic in flavor, and that matures about thirty-four days later.

The present variety most similar to 'Pearl Princess III' peach tree (U.S. Plant Pat. No. 28,505), by having showy blossoms, by being self-fertile, and by producing white flesh peaches that are mostly red in skin color, nearly globose in shape, firm in texture, and sub-acid in flavor, but is distinguished therefrom by having a larger tree, by having globose instead of reniform leaf glands, by blooming about a week later, by requiring more chilling hours, and by producing peaches that are somewhat smaller in size, that are freestone instead of clingstone in type, and that mature about six days earlier. It is to be noted that in 2015 the ripening dates for the California fruit industry were about twenty days earlier than normal, while the 2018 season was near normal. This must be considered when comparing the Jun. 3, 2015, ripening date of 'Pearl Princess III' to the Jun. 14, 2018, ripening date of the present variety.

SUMMARY OF VARIETY

In summary, the present peach variety is characterized by a large size, vigorous, hardy, self-fertile, productive and regular bearing tree. The variety blooms during mid season and requires about 525 chilling hours. The fruit matures under the ecological conditions described in mid June, with first picking on Jun. 14, 2018. The fruit is uniform, medium in size, globose in shape, freestone in type, firm and crisp in texture, mostly red in skin color, white in flesh color, and sub-acidic in flavor.

DRAWING

The accompanying photograph consists of four whole fruits positioned to display the characteristics of the skin color and form, one divided fruit to reveal the flesh and stone, a tip shoot of new leaf growth, typical leaves, and three insets depicting the flower buds and blossoms as they appeared on the tree during the blooming season.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of shipping ripe on Jun. 14, 2018, on the original tree during its eleventh growing season. The blossom and flower descriptions were made the previous blooming season. All major color code designations are by reference to the Inter-Society Color Council, National Bureau of Standards. Common color names are also used occasionally.

PARENTAGE

Seed parent: 'Snow Princess' (U.S. Plant Pat. No. 12,570) peach.

Pollen parent: 'May Princess' (U.S. Plant Pat. No. 18,771) peach.

TREE

Size: Large, reaching and maintaining a height of 14' [4.27 m.] and a spread of 12' [3.66 m.] after eleven growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning necessary.

Fertility: Self-fertile.

Bearing: Regular bearer with no alternate bearing yet observed.

Approximate chilling requirement: 525 hours.

Leaf bud burst: Medium to late, during the end of flowering.

Trunk:

*Size.*—Medium, reaching a maximum diameter of 5½" [139.7 mm.] after the eleventh growing season.

*Texture.*—Shaggy, average roughness.

*Bark color.*—A Moderate yellowish brown [77. m.yBr] and Moderate brown [58. m.Br] variegation with Dark grayish brown [62. d.gy.Br] crevices present.

*Lenticels.*—Approximate Number Per Square Inch: 8. Color: Brownish gray [64. brGy]. Average Size: ¼" [6.4 mm.] in length. The width is typically one fourth as much as the length. Shape: Eye-shaped.

Branches:

*Size.*—Medium, diameter of main scaffold is 3" [76.2 mm.] measured 12" above the crotch, diameter of the limb is 1½" [38.1 mm.] measured 12" above the first fork.

*Texture.*—Medium to smooth on first and second year wood, increasing roughness with age.

*Color.*—1st Year Wood Topside: Grayish red [19. gy.R]. 1st Year Wood Underside: Brilliant yellow green [116. brill.YG]. 2nd Year and Older Wood: A Light grayish brown [60. l.gy.Br] and Moderate brown [58. m.Br] variegation with Brownish orange [54. brO] crevices present.

*Lenticels.*—Number Per Square Inch: About 60 on second year wood. Color: Dark orange yellow [72. d.OY]. Average Size: Medium, 1/16" [1.6 mm.] in length. The width is typically one fourth as much as the length. Shape: Eye-shaped.

Leaves:

*Size.*—Large. Average Length: 6⅛" [155.6 mm.]. Average Width: 1½" [38.1 mm.].

*Arrangement.*—Alternate.

*Thickness.*—Medium.

*Form.*—Elliptical.

*Apex.*—Acuminate.

*Base.*—Mostly acute with an average base angle of 70 degrees.

*Surface.*—Smooth on both sides.

*Color.*—Dorsal Surface: Moderate olive green [125. m.OlG]. Ventral Surface: Moderate yellow green [120. m.YG].

*Red midvein.*—Absent.

*Margin.*—Finely serrate.

*Venation.*—Pinnately net veined.

*Vein color.*—Pale yellow green [121. p.YG].

*Petiole.*—Average Length: ½" [12.7 mm.]. Average Thickness: 1/16" [1.6 mm.]. Color: Moderate olive green [125. m.OlG].

*Stipules.*—Number: Typically two per leaf, up to six per growing tip. Average Length: ¼" [6.4 mm.]. Color: Brilliant yellow green [116. brill.YG] becoming Dark purplish red [259. d.pR] with maturity.

*Glands.*—Number: 1 to 3 per leaf. Position: Somewhat alternate, positioned on the petiole and base of blade. Form: Globose. Size: Medium to small, about 1/64" [0.4 mm.] in diameter.

*Leaf buds.*—Pointed.

Flower buds:

*Hardiness.*—Hardy, with respect to central California blooming season.

*Diameter.*—Typically ⅜" [9.5 mm.] 1 week before bloom.

*Length.*—Typically ⅝" [15.9 mm.] 1 week before bloom.

*Form.*—Not appressed.

*Surface.*—Pubescent.

*Tip color.*—Light pink [4. l.Pk].

Flowers: Perfect, complete, perigynous, usually a single pistil, about thirty stamens, five sepal and petal locations alternately positioned.

*Type.*—Showy, large.

*Average flower diameter.*—1 15/16" [49.2 mm.].

*Average flower depth.*—½" [12.7 mm.] when fully open.

*Number of petals.*—Five, extra petal fragments rarely observed, double blossoms not observed.

*Petal shape.*—Circular to oval.

*Petal margin.*—Entire, slightly wavy.

*Average petal diameter.*—13/16" [20.6 mm.].

*Average petal length.*—13/16" [20.6 mm.].

*Petal apex.*—Rounded.

*Petal base.*—Rounded.

*Petal color.*—Light pink [4. l.Pk] toward the apex and Moderate pink [5. m.Pk] toward the base on both sides.

*Anthocyanin coloration intensity.*—Weak.

*Anther color.*—Moderate reddish orange [37. m.rO] surrounding a Brilliant yellow [83. brill.Y] center at bloom onset.

*Pollen.*—Anthers produce an abundance of Brilliant yellow [83. brill.Y] pollen.

*Stigma color.*—Light greenish yellow [101. l.gY].

*Stigma position.*—Typically located slightly above the nearby anthers.

*Ovary.*—Pubescent.

*Sepal color.*—Grayish purplish red [262. gy.pR] on the outer surface. The inner surface is a somewhat translucent Pinkish white [9. pkWhite] with both Grayish purplish red [262. gy.pR] and Vivid yellow green [115. v.YG] areas visible.

*Sepal length.*—⅜" [9.5 mm.].

*Sepal width.*—5/16" [7.9 mm.].

*Sepal apex.*—Rounded to elliptical to match the sepal length and width.

*Sepal margin.*—Fairly smooth.

*Sepal outer surface.*—Pubescent.

*Average pistil length.*—11/16" [17.5 mm.].

*Average stamen length.*—½" [12.7 mm.].

*Fragrance.*—Moderate.

*Blooming period.*—Medium, blooms about six days after 'Pearl Princess III' (U.S. Plant Pat. No. 28,505) peach.

*Onset of bloom.*—One percent on Feb. 21, 2018.

*Date of full bloom.*—Mar. 3, 2018.

*Duration of bloom.*—One to two weeks, dependent on ambient temperature.

*Bloom density.*—Medium to heavy.

*Number per cluster.*—1 to 3 with single flowers most common.

FRUIT

Maturity when described: Shipping ripe, Jun. 14, 2018.

Date of first picking: Jun. 14, 2015.

Date of last picking: Jun. 23, 2015.

Size: Uniform, medium.

*Average diameter axially.*—3" [76.2 mm.].

*Average diameter across suture plane.*—3" [76.2 mm.].

*Average diameter across cheek plane.*—3" [76.2 mm.].

*Typical weight.*—8.6 ounces [244 grams].

Form: Uniform, very globose, symmetrical.

*Longitudinal section form.*—Round.

*Axial view.*—Round.

Suture: A shallow trough extending from the base to just beyond the pistil point.

*Near the base.*—A shallow groove.

*Along the side.*—A very shallow trough.

*Near the apex.*—A moderate trough.

Ventral surface: Rounded.

Lips: Lipped on both sides. Lips are slightly unequal.

Cavity: Flaring, elongated in the suture plane, suture showing on one side, Pale greenish yellow [104. p.gY] stem markings typical.

*Depth.*—½" [12.7 mm.].

*Breadth.*—1¼" [31.8 mm.].

Base: Slightly truncate, moderately cordate if viewed parallel to the suture.

Apex: Rounded.

Pistil point: Apical, short with a typical length of 1/16" [1.6 mm.].

Stem: Medium.

*Average length.*—⅜" [9.5 mm.].

*Average width.*—3/16" [4.8 mm.].

Skin:

*Thickness.*—Medium.

*Surface.*—Pubescent.

*Density of the pubescence.*—Medium to light.

*Down.*—Short, does not roll up when rubbed.

*Tenacity.*—Tenacious to flesh.

*Astringency.*—Non-astringent.

*Tendency to crack.*—None observed.

*Color.*—Very deep red [14. v.deep R] over a Strong pink [2. s.Pk] background with a few Yellowish white [92. yWhite] areas where sun protected.

Flesh:

*Color.*—Yellowish white [92. yWhite] with Strong red [12. s.R] flecking toward the skin.

*Surface of pit cavity.*—Covered with Pale greenish yellow [104. p.gY] and Moderate pink [5. m.Pk] fibers.

*Amygdalin.*—Scant.

*Juice.*—Moderate.

*Texture.*—Firm, crisp, melting.

*Fibers.*—Fine.

*Ripens.*—Fairly even, slightly earlier toward the apex.

*Flavor.*—Sub-acidic, mild, typically 13 brix.

*Aroma.*—Moderate.

*Eating quality.*—Good.

STONE

Type: Freestone.
Form: Elliptical.
Hilum: Narrow.
Base: Rounded.
Apex: Acute.
Sides: Mostly Equal.
Tip: Sharp, ⅛" [3.2 mm.] in length.
Surface: Irregularly furrowed near the apex, pitted toward the base.
Ridges: Rounded.
External color: Dark orange yellow [72. d.OY].
Pit wall color when cracked: Pale orange yellow [73. p.OY].
Cavity surface color: Strong yellowish brown [74. s.yBr].
Average pit wall thickness: ¼" [6.4 mm.].
Average length: 1 11/16" [42.9 mm.].
Average width: 1⅛" [28.6 mm.].
Average breadth: ¾" [19.1 mm.].
Tendency To split: None observed.
Kernel:

*Form.*—Oval.
*Skin color.*—Pale yellow [89. p.Y] when first removed.
*Pellicle color.*—Moderate reddish brown [43. m.rBr].
*Vein color.*—Light yellow [86. l.Y].
*Taste.*—Bitter.
*Viable.*—Yes.
*Average length.*—11/16" [17.5 mm.].
*Average width.*—7/16" [11.1 mm.].
*Amygdalin.*—Moderate.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of peach tree, substantially as illustrated and described, that is most similar to 'Pearl Princess III' peach tree (U.S. Plant Pat. No. 28,505), by having showy blossoms, by being self-fertile, and by producing white flesh peaches that are mostly red in skin color, nearly globose in shape, firm in texture, and sub-acid in flavor, but is distinguished therefrom by having a larger tree, by having globose instead of reniform leaf glands, by blooming about a week later, by requiring more chilling hours, and by producing peaches that are somewhat smaller in size, that are freestone instead of clingstone in type, and that mature about six days earlier.

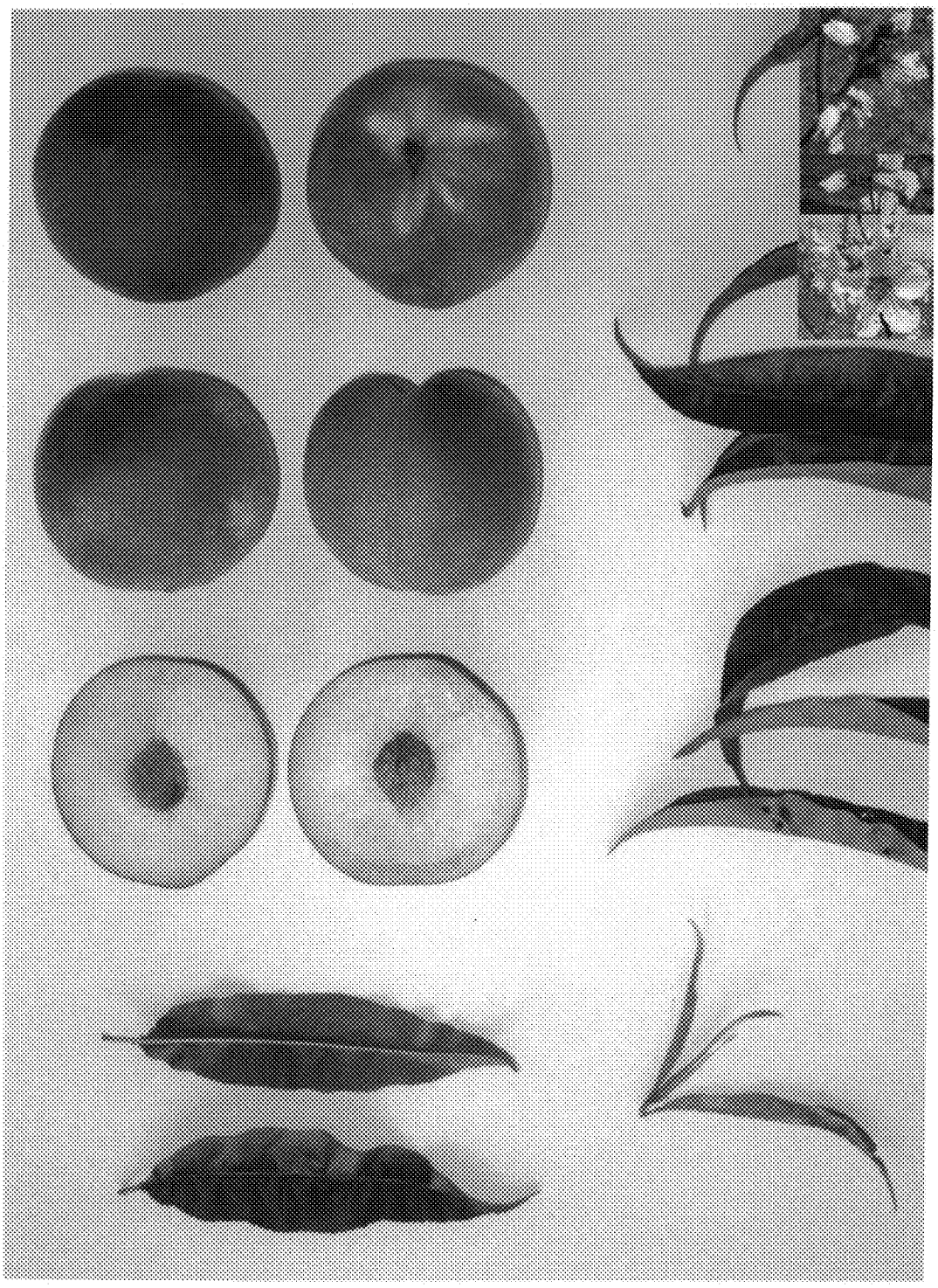

* * * * *